(12) United States Patent
Allen et al.

(10) Patent No.: US 9,033,709 B1
(45) Date of Patent: May 19, 2015

(54) DENTAL ATTACHMENT ASSEMBLY CAP AND METHOD OF USE

(71) Applicant: Zest IP Holdings, LLC, Escondido, CA (US)

(72) Inventors: Richard Robert Allen, Oceanside, CA (US); Christopher Michael Gervais, San Marcos, CA (US)

(73) Assignee: ZEST IP HOLDINGS, LLC, Escondidoca, CA (US)

( * ) Notice: Subject to any disclaimer, the term of this patent is extended or adjusted under 35 U.S.C. 154(b) by 0 days.

(21) Appl. No.: 14/298,818

(22) Filed: Jun. 6, 2014

(51) Int. Cl.
*A61C 8/00* (2006.01)

(52) U.S. Cl.
CPC ............. *A61C 8/0053* (2013.01); *A61C 8/0062* (2013.01)

(58) Field of Classification Search
CPC .. A61C 8/0053; A61C 8/0054; A61C 8/0057; A61C 8/0059; A61C 8/0062; A61C 8/005
USPC .......................................... 433/172, 173, 174
See application file for complete search history.

(56) References Cited

U.S. PATENT DOCUMENTS

| | | | | |
|---|---|---|---|---|
| 1,422,452 | A * | 7/1922 | Lace | 433/183 |
| 4,324,549 | A * | 4/1982 | Madray | 433/169 |
| 4,488,874 | A * | 12/1984 | Soifer | 433/173 |
| 5,030,094 | A * | 7/1991 | Nardi et al. | 433/169 |
| 5,098,295 | A * | 3/1992 | Durr et al. | 433/172 |
| 6,030,219 | A * | 2/2000 | Zuest et al. | 433/181 |
| 6,203,325 | B1 * | 3/2001 | Honkura et al. | 433/177 |
| 6,299,447 | B1 * | 10/2001 | Zuest et al. | 433/172 |
| 6,981,871 | B2 * | 1/2006 | Mullaly et al. | 433/172 |
| 8,512,039 | B2 * | 8/2013 | Mullaly et al. | 433/174 |
| 2002/0177103 | A1 * | 11/2002 | Pelak | 433/173 |
| 2006/0014120 | A1 * | 1/2006 | Sapian | 433/173 |

* cited by examiner

*Primary Examiner* — Ralph Lewis
(74) *Attorney, Agent, or Firm* — Procopio, Cory, Hargreaves & Savitch LLP; Noel C. Gillespie (57) ABSTRACT

A dental attachment assembly and method anchors a dental appliance with an implant and has an abutment member attached to the implant, a retention member in releasable snap engagement with the abutment member, and a cap secured in a recess of the dental appliance and in releasable swivel engagement with the retention member to position and secure the dental appliance onto the implant. The cap includes a cavity with a rounded, concave inner surface which engages with the retention member, an interior top surface of the cavity with a concave recess extending radially along an outer periphery of the interior top surface of the cavity to allow for rotation of the retention member within the cap. A central portion of the interior top surface of the cavity surrounded by the concave recess therefore protrudes vertically into the cavity to minimize vertical displacement of the retention member as it rotates.

10 Claims, 15 Drawing Sheets

DENTAL ATTACHMENT ASSEMBLY CAP AND METHOD OF USE

BACKGROUND

1. Field of the Invention

Devices and methods provided herein relate to a dental attachment assembly for anchoring a dental appliance with a base structure such as a dental implant, and more specifically to an attachment assembly with a cap for positioning and retaining the dental appliance.

2. Related Art

Dental anchoring assemblies are known in which a female part is provided for attachment to a root, implant, or adjacent tooth, and a male part is engaged in a recess in a dental appliance, the male and female parts having mating, snap engageable formations for releasably securing the male part to the female part. For example, in U.S. Pat. No. 5,417,570, to Zuest, the female part has a socket and the male part has a head for snap engagement in the socket. However, users may find it difficult to properly locate the male head in the female socket, such that the head may hit the periphery of the socket in some cases. Repeated impacts of this nature may damage the retentive head of the male, causing it to lose some of its retention ability.

U.S. Pat. Nos. 6,030,219 and 6,299,447 of Zuest et al., incorporated herein by reference in their entirety, describe dental attachment assemblies in which the male part has a skirt for snap engagement over an outer locating surface of the female or abutment member. The male part may also have a central stem for snap engagement in a socket in the female part, providing both inner and outer retention surfaces, and therefore increased retention force. It is also easier to locate the male part properly over the female part.

U.S. Pat. No. 6,981,871, to Zuest, incorporated herein by reference in its entirety, describes an outer locating surface that has at least two axially spaced retention surfaces for mating, snap engagement with corresponding spaced snap engagement formations on the inner surface of a cap secured in a dental appliance to provide a stacked, external retention between the abutment and retention members.

However, it is desirable to not only improve the retention of the components of the dental attachment assemblies but to also improve their adjustability.

SUMMARY

Embodiments described herein provide for a dental attachment assembly and method which anchors a dental appliance with an implant or other base structure, the dental attachment assembly including an abutment member attached to the implant or base structure, a retention member in releasable snap engagement with the abutment member, and a cap secured in a recess of the dental appliance and configured in releasable swivel engagement with the retention member to position and secure the dental appliance onto the implant. The cap includes a cavity with a rounded, concave inner surface which engages with the retention member, and an interior top surface of the cavity with a concave recess extending radially along an outer periphery of the interior top surface of the cavity to allow for rotation of the retention member within the cap. A central portion of the interior top surface of the cavity surrounded by the concave recess therefore protrudes vertically into the cavity to minimize vertical displacement of the retention member as it rotates within the cap.

In one embodiment, a cap of a dental attachment assembly comprises an outer surface shaped to engage with a recess in a dental appliance; a rounded, concave inner surface defining a cavity to receive a swivel engagement with a retention member; and an interior top surface of the cavity with a concave recess extending radially along an outer periphery of the interior top surface of the cavity.

In a further embodiment, a dental attachment assembly comprises an abutment member with a first end shaped to attach to a tooth root, implant or adjacent tooth, and a second end with an outer locating surface; a retention member having a first end and a skirt extending from the first end defining an inner surface for engagement over the outer locating surface of the abutment member; and a cap with a rounded, concave inner surface defining a cavity to receive a swivel engagement with the retention member; wherein an interior top surface of the cavity includes a concave recess extending radially along an outer periphery of the interior top surface of the cavity.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for a dental attachment assembly and method which anchors a dental appliance with an implant or other base structure, the dental attachment assembly including an abutment member attached to the implant or base structure, a retention member in releasable snap engagement with the abutment member, and a cap secured in a recess of the dental appliance and configured in releasable swivel engagement with the retention member to position and secure the dental appliance onto the implant. The cap includes a cavity with a rounded, concave inner surface which engages with the retention member, and an interior top surface of the cavity with a concave recess extending radially along an outer periphery of the interior top surface of the cavity to allow for the retention member to swivel within the cap. A central portion of the interior top surface of the cavity surrounded by the concave recess therefore protrudes vertically into the cavity to minimize vertical displacement of the retention member as it rotates within the cap.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

The dental attachment assembly described herein simplifies the process of attaching a dental appliance to a base structure such as an implant by providing greater flexibility and movement of the dental attachment assembly as the assembly is being positioned onto the implant. The creation of a concave recess extending radially along an outer periphery of the interior top surface of the cavity allows the retention element to rotate or swivel within the cap at a greater angle, which increases the allowable angle correction at which the assembly can be fitted onto the abutment while limiting vertical displacement of the retention element. There are many anatomical conditions that dictate implants be placed at various angulations which exceed the angle correction capabilities of current prosthetic options. This improved cap and assembly provides greater ease of use when positioning and adjusting a dental appliance in a person's mouth.

A. Dental Attachment Assembly

Figure 1A:
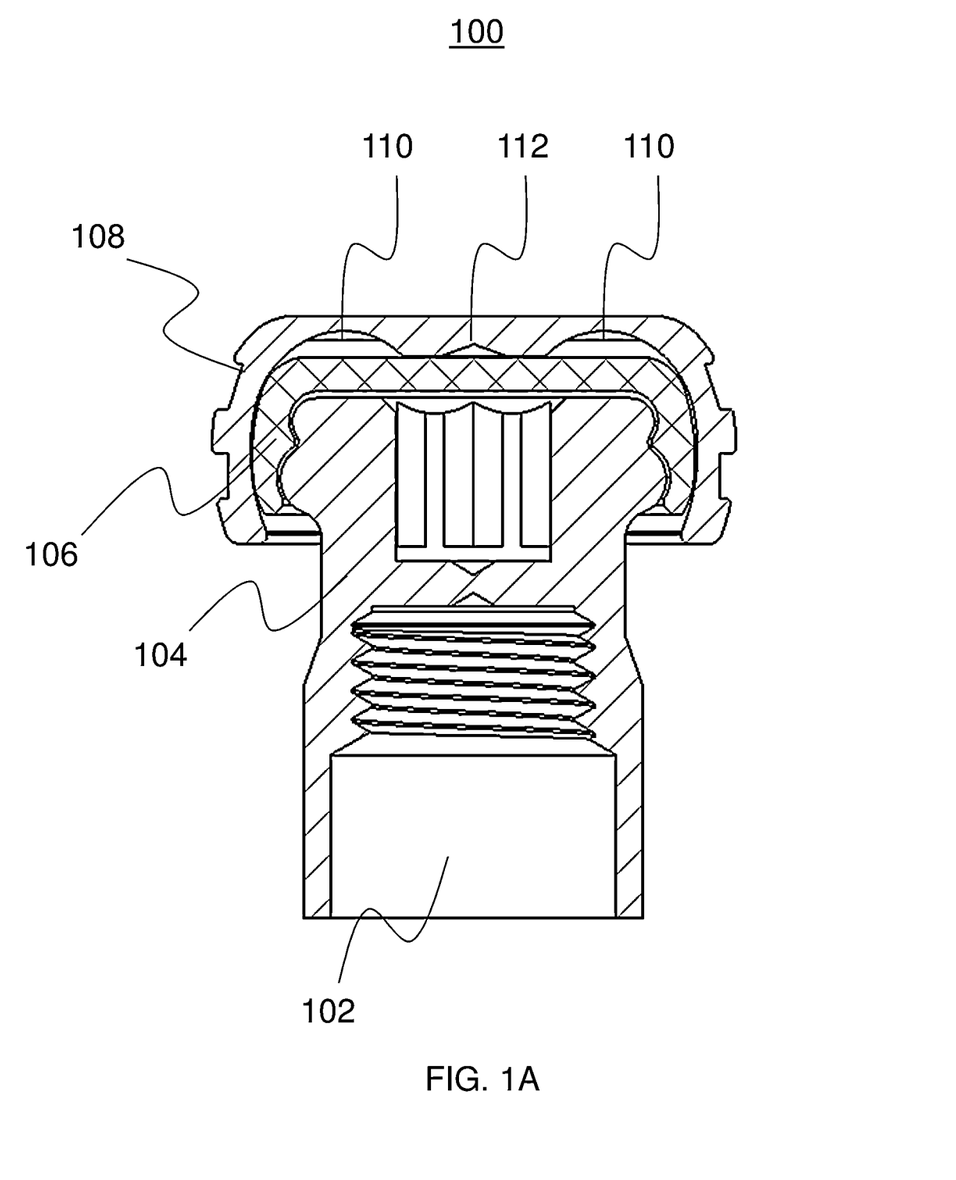
FIG. 1A is a side cutout view of a dental attachment assembly, according to an embodiment of the invention.
Figure 14:
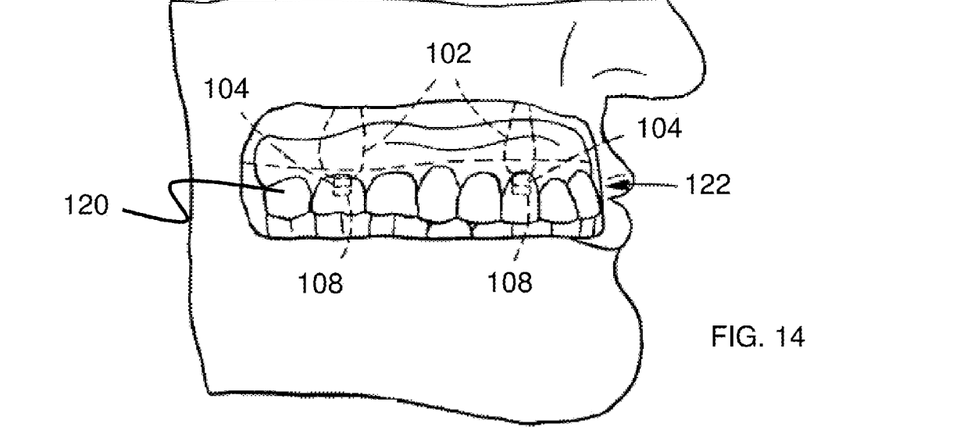
FIG. 14 is a side view illustration of the dental attachment assembly after securing the dental appliance in a patient's mouth, according to an embodiment of the invention.
Figure 15:
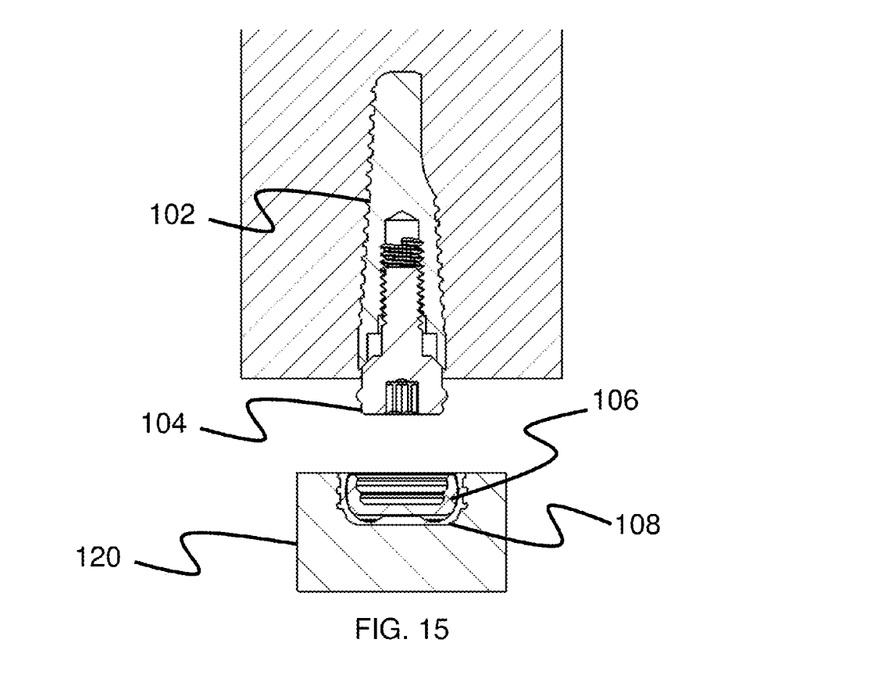
FIG. 15 is a side view illustration of the process of anchoring the cap and retention member onto the abutment of the dental attachment assembly, according to an embodiment of the invention.

FIG. 1A illustrates one embodiment of the dental attachment assembly 100 attached with an implant 102 that may be anchored to a bone or other base structure (not shown) such as a tooth root. An abutment 104 of the dental attachment assembly 100 is attached to one end of the implant 102 such that the abutment 104 is visible above the tissue typically surrounding the implant 102. A retention member 106 is then connected with a top portion of the abutment 104 via a releasable snap engagement or other retention means described below. A cap 108 with a rounded, concave inner surface defining a cavity is then fitted in swivel engagement over the retention member 106 to allow the cap 108 to swivel with respect to the retention member 106 and abutment 104. The cap 108 is secured in a recess of a dental appliance (as shown in FIGS. 14 and 15) such that the cap 108 retains the retention member 106 which engages with the abutment 104 when the dental appliance is being fitted onto the abutment. The engagement of the cap 108 with the retention member 106 defines a swivel joint which permits the cap 108 and thus the dental appliance to swivel with respect to the retention member 106, abutment 104 and implant 102.

Figure 1B:
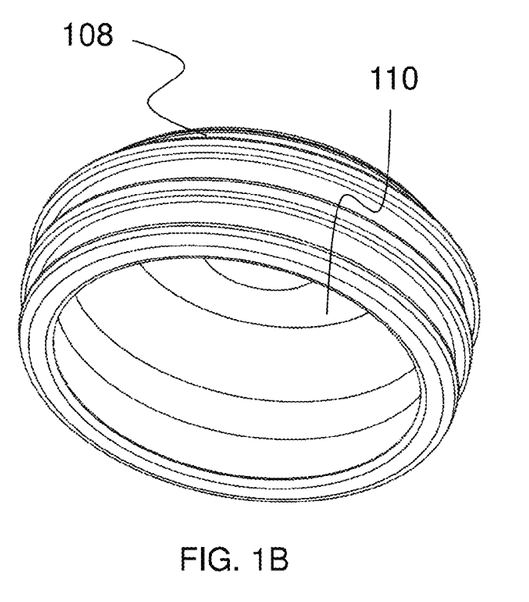
FIG. 1B is an isometric view illustration of the cap of the dental attachment assembly, according to one embodiment of the invention.
Figure 1C:
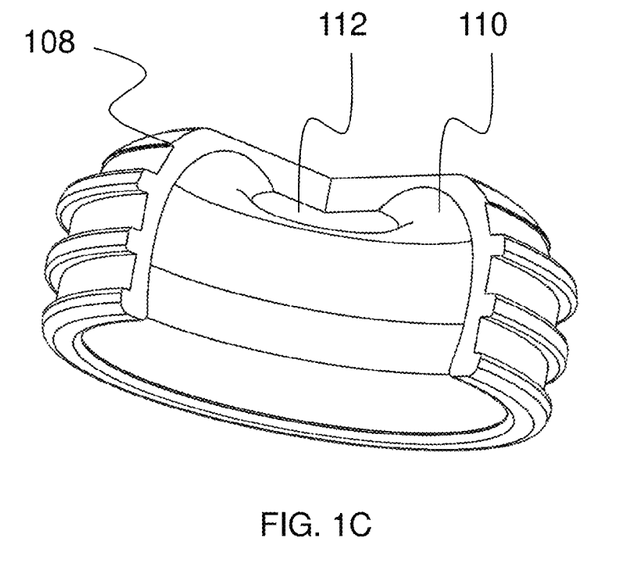
FIG. 1C is an isometric cutout view illustration of the cap of the dental attachment assembly, according to one embodiment of the invention.

As shown in FIG. 1A and more clearly in the isometric views in FIG. 1B and FIG. 1C, in one embodiment, an interior top surface of the cap 108 is configured with a concave recess 110 extending radially along an outer periphery of the interior top surface of the cavity. The concave recess 110 allows the cap 108 to swivel at a much greater angle with respect to the retention member 106 and abutment 104, which makes it easier for a person to secure the dental appliance onto the abutment 104. A central portion 112 of the interior top surface of the cap 108 protrudes vertically into the cap cavity and minimizes vertical displacement between the retention member 106 and the cap 108 that would have occurred without the presence of the central portion 112. In this exemplary embodiment, the cap is approximately 1.9 millimeters in height, although one of skill in the art will appreciate that the dimensions of the cap may vary.

In the embodiment illustrated in FIG. 1A, the retention member 106 is retained by a skirt (or side wall) that projects from one end of the cap 108 for releasable engagement of the retention member 106 with the cap 108, as disclosed in U.S. Pat. No. 6,981,871, incorporated herein by reference in its entirety. The outer locating surface of the abutment 104 has at least two axially spaced retention surfaces for mating, snap engagement with corresponding spaced snap engagement formations on the inner surface of the retention member 106, to provide a stacked, external retention between the abutment 104 and retention member 106.

B. Cap Design

Figure 2:
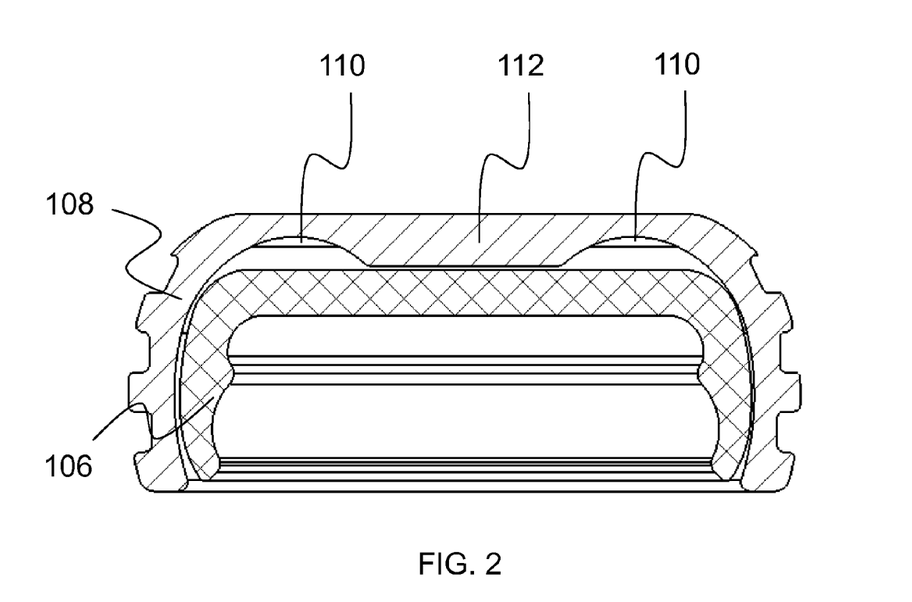
FIG. 2 is a side cutout view illustration of a cap and retention member of the dental attachment assembly, according to an embodiment of the invention.

FIG. 2 illustrates a side cutout view of the cap 108 and retention member 106 in a non-swiveled position, which more clearly illustrates how the retention member 106 fits within the cavity of the cap 108 when no swiveling has occurred. The retention member 106 is in contact with the central portion 112 of the interior top surface of the cap 108. Outer side walls of the retention member 106 are generally curved to match the curved surface of the inner side walls of the cap 108, and they may be in direct contact at a portion of the side walls at any one position to allow for ease of swivel without an excessive amount of friction.

Figure 3:
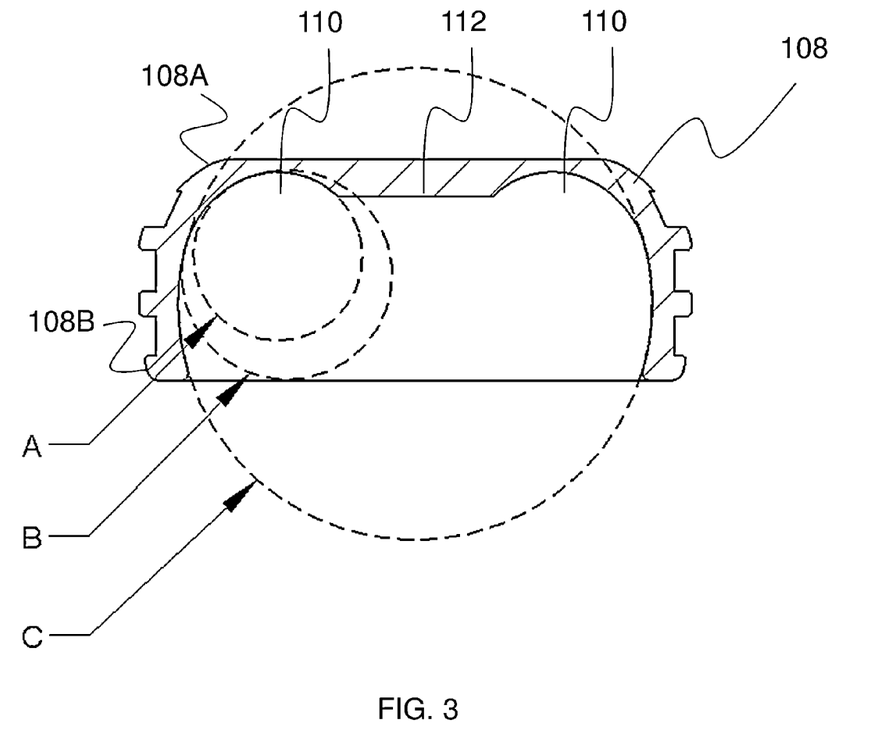
FIG. 3 is a side cutout view illustration of the cap illustrating consecutive tangent circle arcs which are used to create an angle of a concave recess on an interior wall of the cap, according to an embodiment of the invention.
Figure 4:
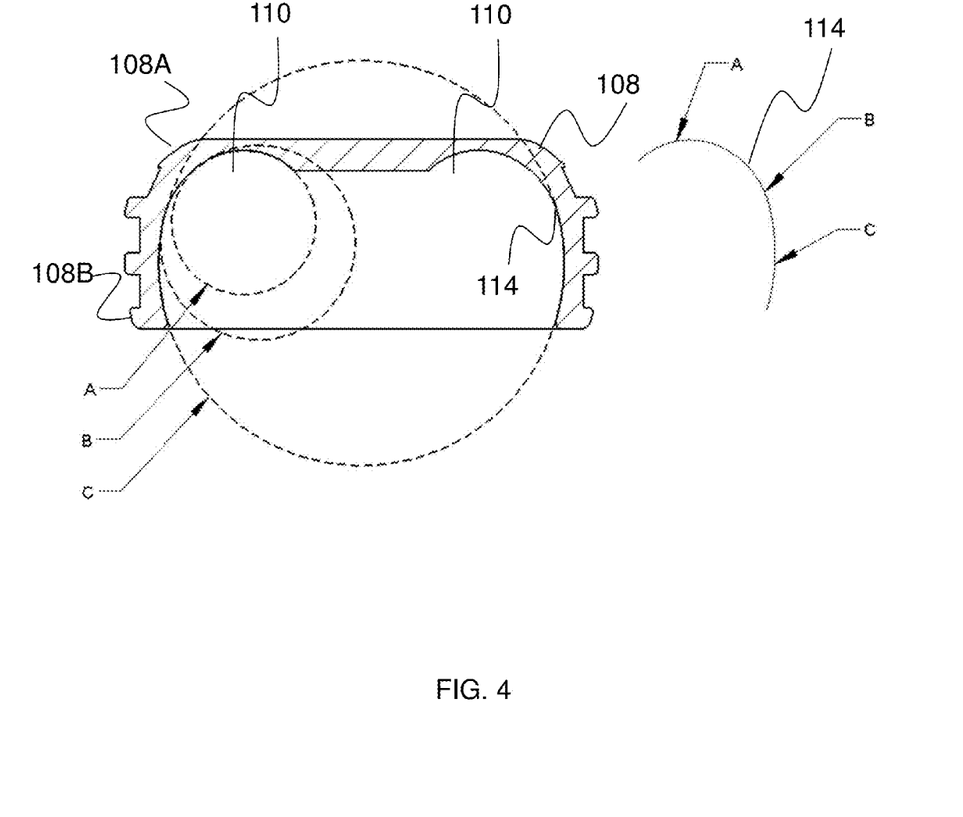
FIG. 4 is a side cutout view illustration of the cap illustrating an angle of the concave recess, according to an embodiment of the invention.
Figure 5:
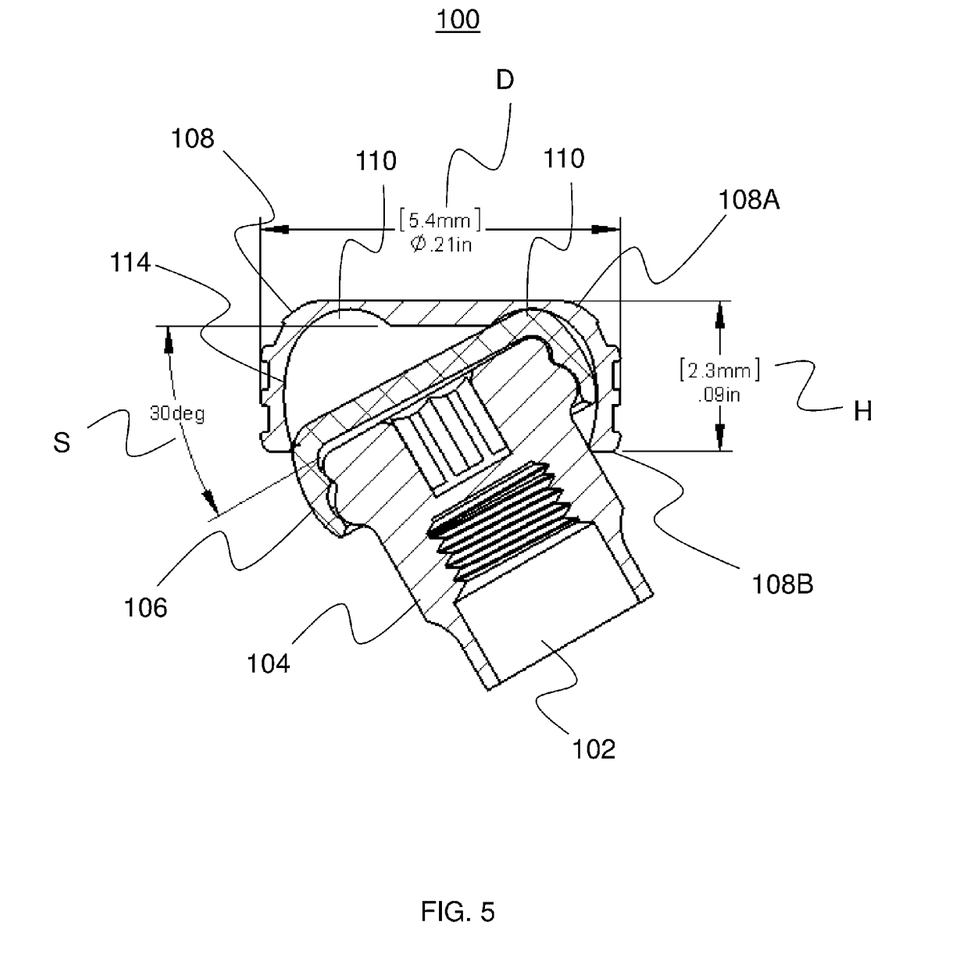
FIG. 5 is a side cutout view of a dental attachment assembly in a fully swiveled position, according to an embodiment of the invention.

In one embodiment, the concave recess 110 is specifically designed with a curvature 114 which may be formed using a series of consecutive tangent circular arcs formed from multiple circles of varying radii, as illustrated in FIG. 3 and FIG. 4. In the embodiment illustrated herein, circles A, B, and C represent portions of the tangent circular arcs used to derive the curve 114, although any plurality of circles may be used. The circles A, B, and C are arranged from large-to-small diameter from a bottom portion 108B of the cap to a top portion 108A of the cap to form the varying angles of the curve 114. As illustrated in FIG. 5, the curve 114 is designed to optimize the swivel of the cap 108 around the retention member 106 while maintaining engagement of the retention member 106 within the cap 108. Varying diameters of each of the circles may be used as long as the diameters are arranged from large-to-small from a bottom-to-top direction along the interior side wall of the cap. In the exemplary embodiment of FIG. 3, the concave recess 110 is formed from circles A, B, and C with diameters of 0.067, 0.083 and 0.186 inches, respectively. Circle C has a diameter which intersects the concave recess 110 on an opposing side of the cap, which therefore defines the diameter of the cap cavity. Each curvature of each circle intersects with a different portion of the concave recess 110 to form a curved surface 114 of varying degrees of curvature, as shown in FIG. 4. In this embodiment, the curve 114 is formed from circles with radii values of 0.34, 0.42 and 0.93 inches at various points along the curve, which correspond to the diameters in the example provided above.

FIG. 5 illustrates one embodiment of the retention member 106 and abutment 104 in a fully swiveled position within the cap 108, where a portion of the retention member 106 has swiveled into the concave recess 110 in the cap 108. The opposing side of the retention member 106 has swiveled downward to the point that it is still retained within the cap 108, which illustrates the complete range of swivel of the cap 108 in one direction. In this embodiment, the range of swivel S is approximately 30 degrees with a cap having a diameter D of approximately 5.4 millimeters (mm) and a height H of approximately 2.3 mm, although one of skill in the art will appreciate that these dimensions may be varied and still achieve the same degree of rotation. The range of rotation may reasonably extend to approximately 32 degrees and could be extended up to approximately 40 degrees if the dimensions of the cap, retention member and abutment are altered to allow for greater rotation—for example by increasing the height of the cap and reducing the diameter of the abutment.

Figure 6:
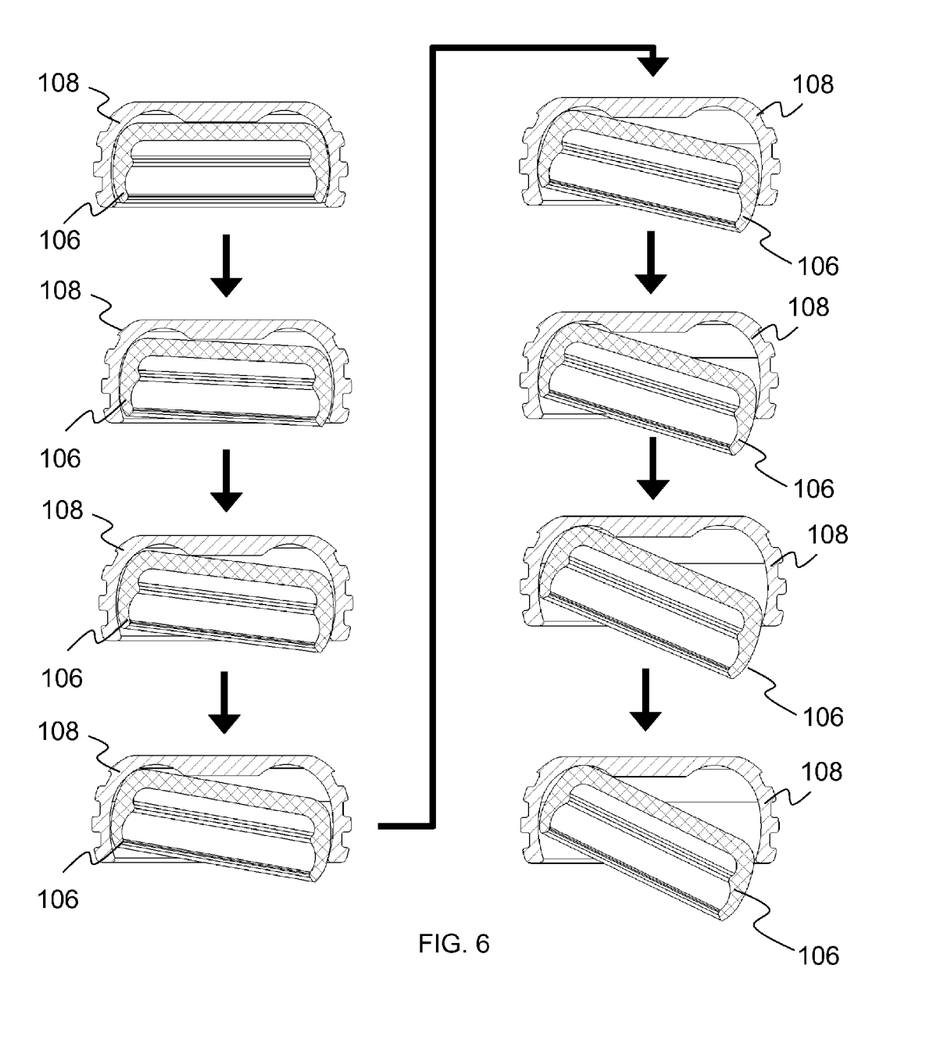
FIG. 6 is a side cutout view illustration of a progression of the retention member swiveling from an un-swiveled position to a fully swiveled position, according to an embodiment of the invention.
Figure 7:
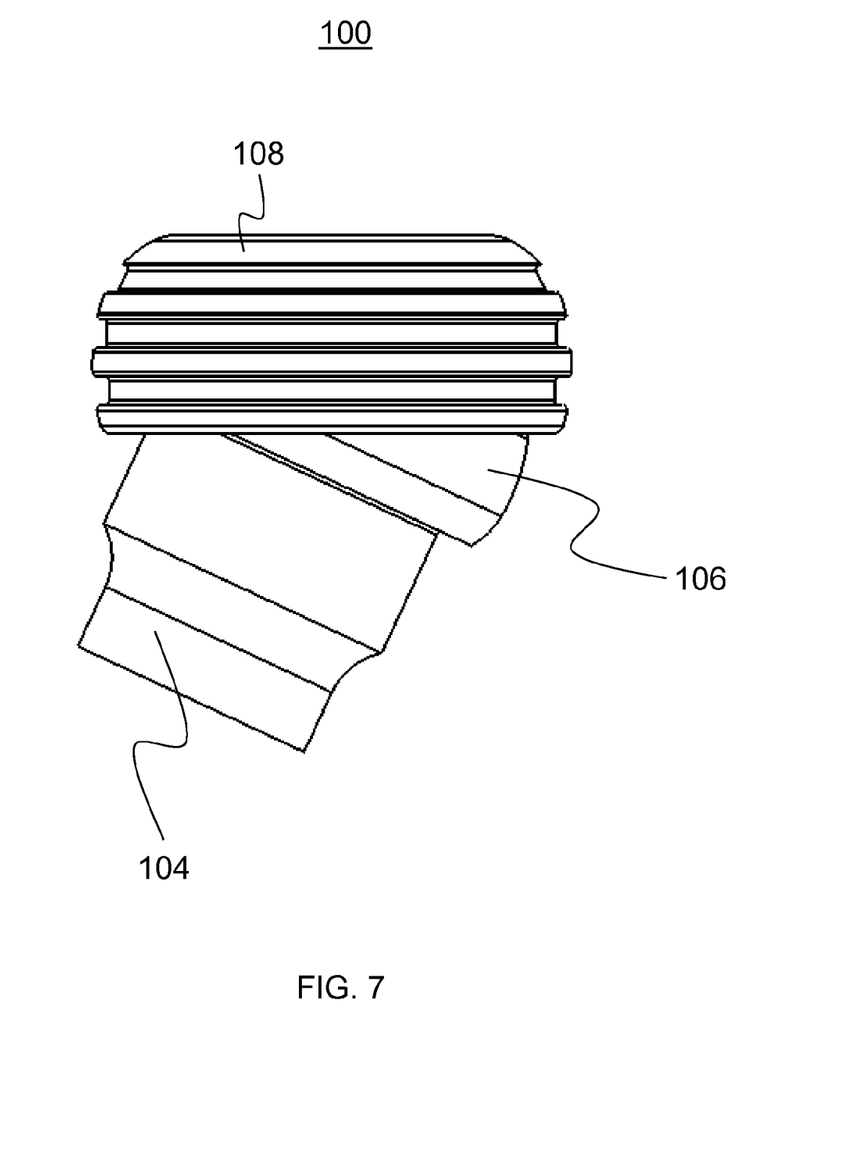
FIG. 7 is a side view illustration of the dental attachment assembly in a fully swiveled position, according to an embodiment of the invention.

FIG. 6 illustrates a series of drawings of the cap 108 and retention member 106 as the retention member 106 begins to swivel from a non-swiveled position to a fully-swiveled position, and FIG. 7 illustrates a side view illustration of the complete dental attachment assembly in the fully-swiveled position. With the cap 108 inserted into a recess of a dental appliance, the amount of swivel is therefore translated to the dental appliance as the dental appliance is being attached to the assembly, allowing for a great deal of flexibility as a dental professional or the patient attaches the appliance to the abutment.

C. Alternative Assemblies

Figure 8:
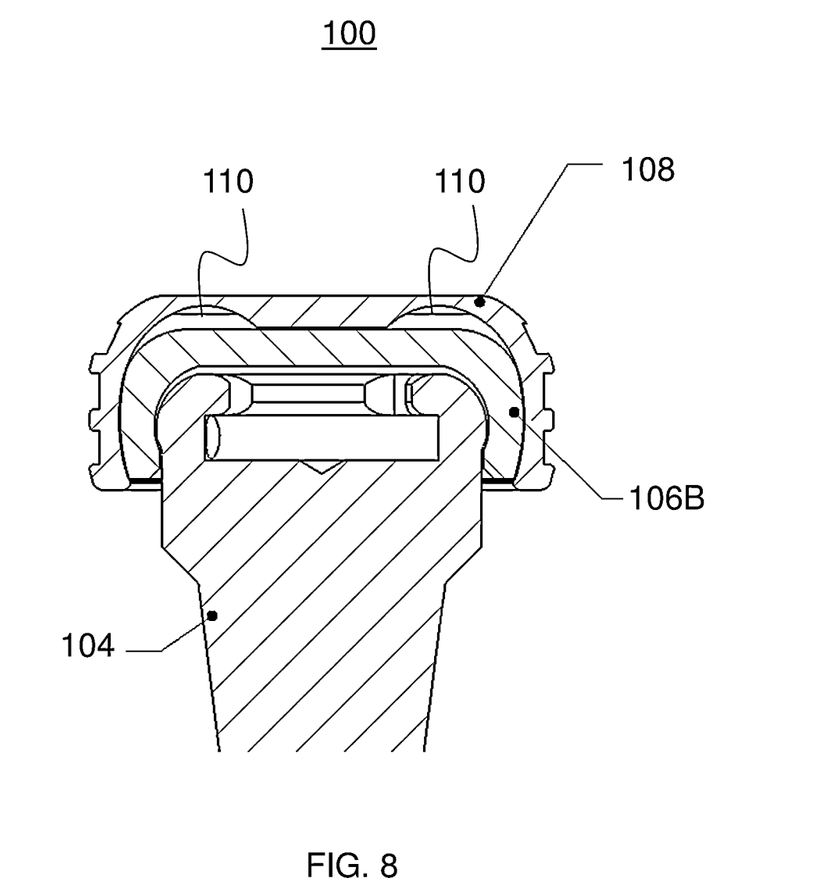
FIG. 8 is a side cutout view illustration of the cap and an alternate design of the retention member and an alternate design of an abutment, according to an embodiment of the invention.

FIG. 8 illustrates an alternate embodiment of the dental attachment assembly with an abutment 104 and retention member 106B which are engaged using a snap engagement between the external surface of the abutment 104 and the internal surface of the retention member 106B. In this embodiment, the cap 108 retains the radial concave recess 110, but the abutment 104 has only one retention surface on the outer portion of the abutment for mating with the corresponding annular concavity on the retention member 106B. The cap 108 therefore still provides the added rotational flexibility with the retention member 106B and abutment 104 even though the retention mechanism is different.

Figure 9:
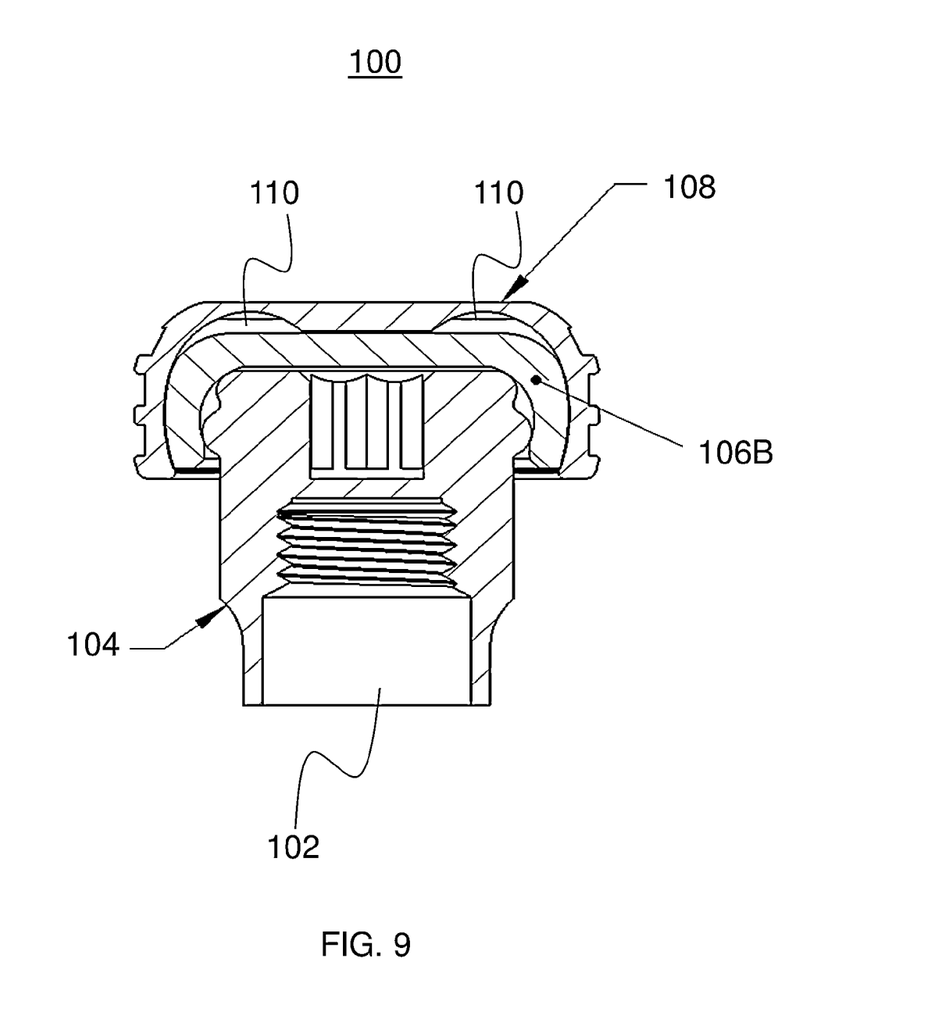
FIG. 9 is a side cutout view illustration of the cap and an alternate design of the retention member and an abutment, according to an embodiment of the invention.

FIG. 9 illustrates another alternative embodiment where the abutment 104 is provided with axially-spaced retention surfaces, although the retention member 106B is not configured with corresponding annular grooves. Nevertheless, the retention member 106B is still capable of retaining the abutment 104 and providing for full rotation within the cap 108 within the concave recess 110.

Figure 10A:
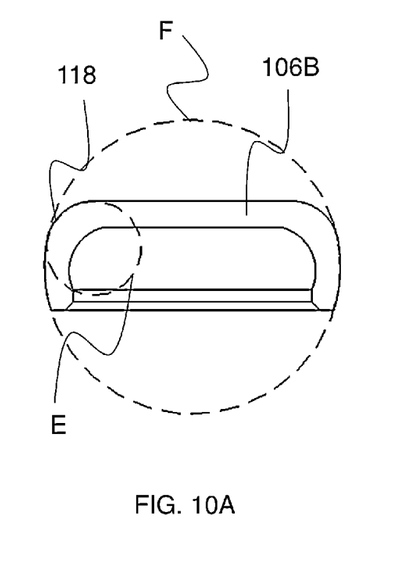
FIGS. 10A and 10B are side-by-side comparisons of diameters of circles which define an outer surface of two configurations of the retention members, according to an embodiment of the invention.
Figure 10B:
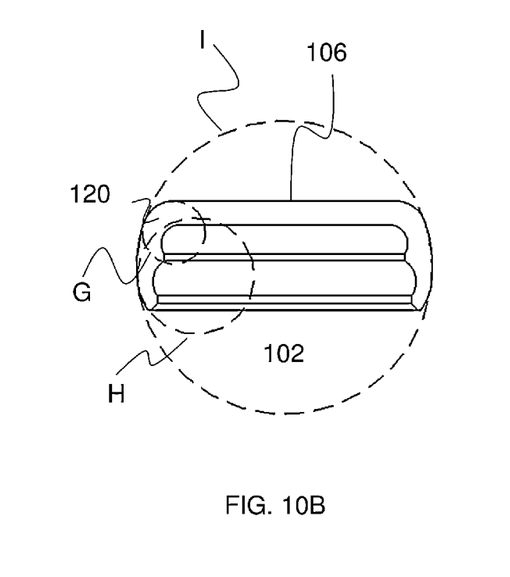

FIG. 10A illustrates the design of the curvature of an outer curved surface 118 of the retention member 106B without annular grooves for retaining the abutment, while FIG. 10B illustrates the design of the curvature of an outer curved surface 120 of the retention member 106 with annular grooves for retaining the abutment. The measurements provided demonstrate that various geometry configurations can be designed so that the retention member will swivel within the cap. The design can be optimized to provide for movement of the retention member in the cap free from friction or can be designed with a small amount of resistance, while still allowing for swiveling within the cap. In FIG. 10A, the outer curved surface 118 of retention member 106B is configured from a circle E with a diameter of 0.060 inches and a circle F with a diameter of 0.187 inches. In FIG. 10B, the outer curved surface 120 of retention member 106 is configured from a circle G with a diameter of approximately 0.040 inches, a circle H with a diameter of approximately 0.074 inches, and a circle I with a diameter of approximately 0.186 inches. The slight variances in measurement illustrate that both configurations of retention members are capable of fitting within the cap and achieving the same degree of swivel provided by the concave recess 110.

Figure 11:
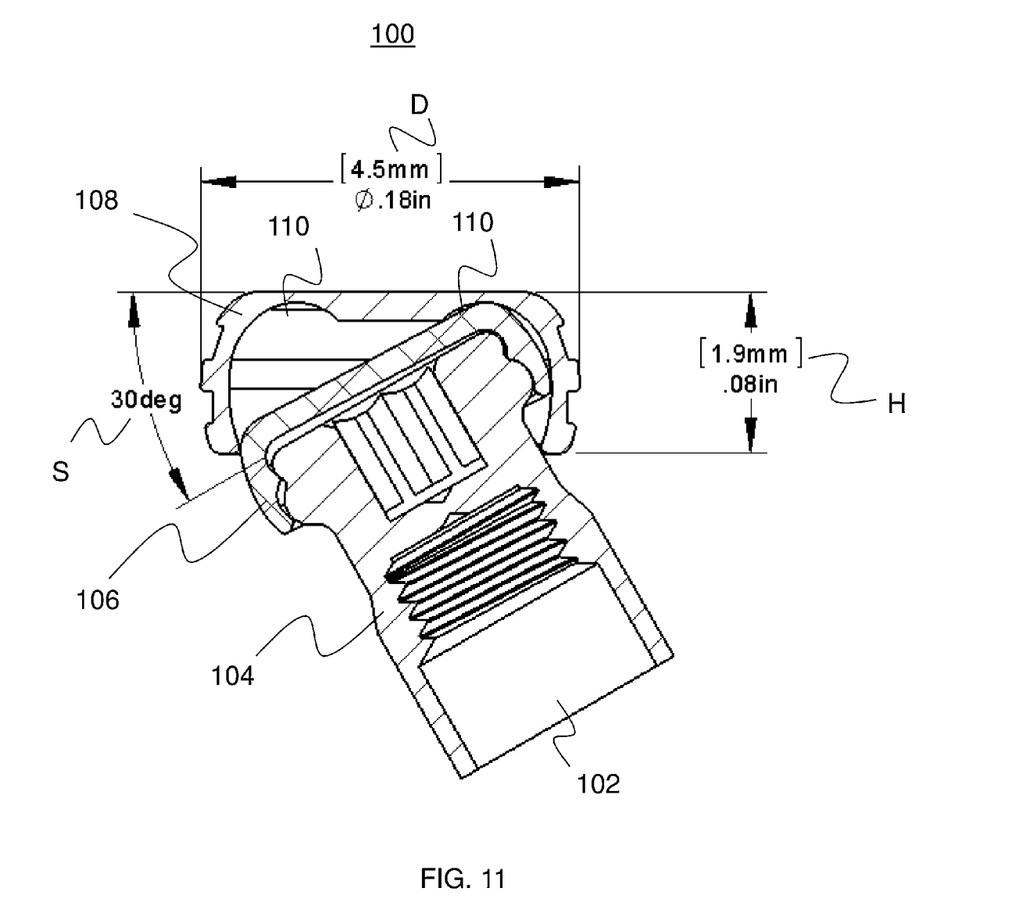
FIG. 11 is a side cutout view illustration of a different-sized configuration of the dental attachment assembly, according to an embodiment of the invention.
Figure 12:
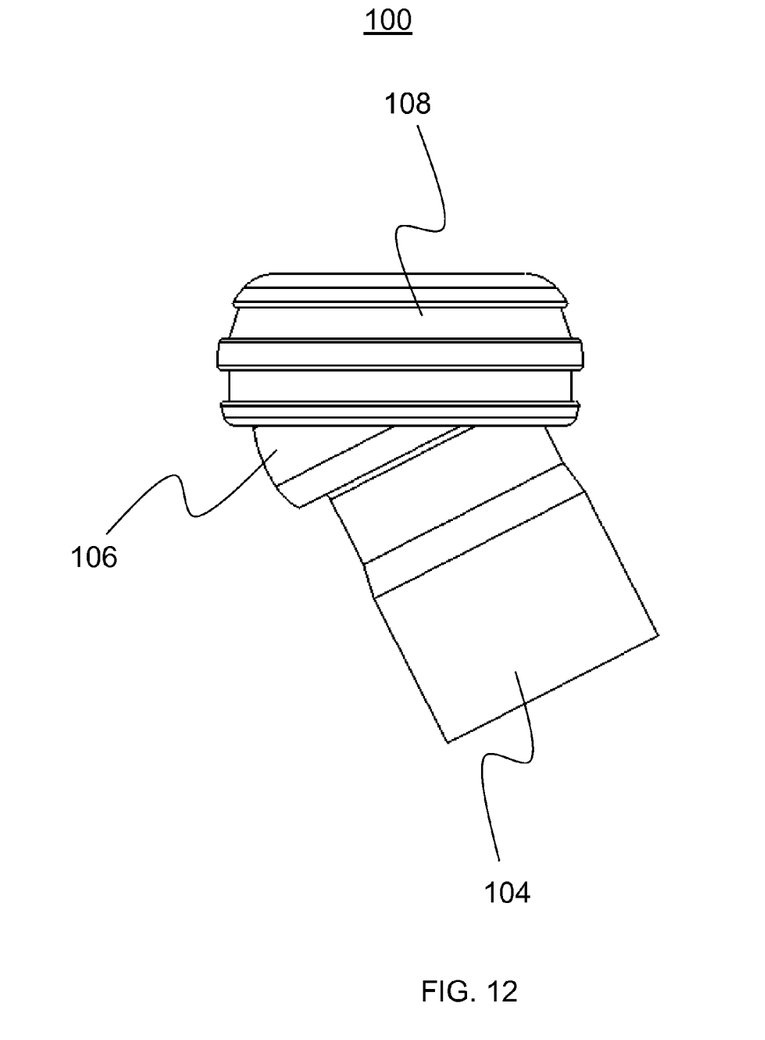
FIG. 12 is a side view illustration of the different-sized configuration of the dental attachment assembly in a fully swiveled position, according to an embodiment of the invention.

FIG. 11 illustrates a dental attachment assembly 100 of a smaller size than the embodiment illustrated in FIG. 1A and FIG. 5. Despite the smaller size, the angle of swivel S is still approximately 30 degrees, indicating that different sized attachment assemblies may be made with the same properties for use in different sections of the mouth where larger assemblies may be impractical. FIG. 12 illustrates a side view illustration of the smaller dental attachment assembly 100 in the fully-swiveled position.

D. Method of Use

Figure 13:
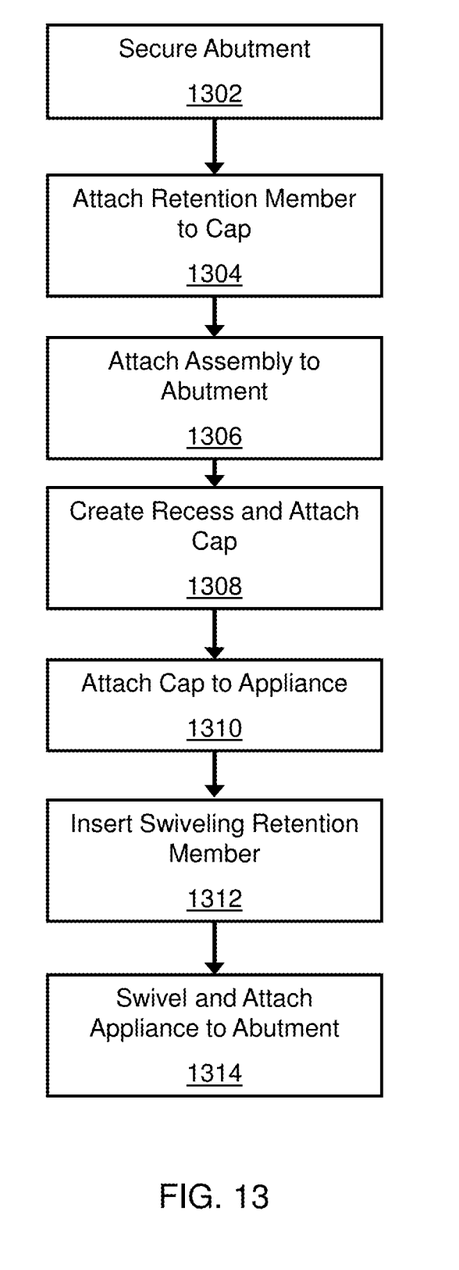
FIG. 13 is a flow diagram illustrating an example process for anchoring a dental appliance in a patient's mouth, according to an embodiment of the invention.

FIG. 13 illustrates one embodiment of a method of attaching a dental appliance to an implant using the dental attachment assembly described herein. In a first step 1302, an abutment is secured to an implant or other root structure that will support the dental appliance. Next, a non-swiveling retention member is inserted into the cap (step 1304), and this assembly is then attached to the abutment in step 1306. In step 1308, the dental appliance is modified with a recess placed in the appropriate position to accept the non-swiveling retention member and cap assembly in preparation for attachment, and in step 1310, the cap is bonded into the recess in the dental appliance. In step 1312 the non-swiveling retention member is removed from the cap and a swiveling retention member is inserted into the cap. In step 1312, the dental appliance may be engaged onto the abutment by the snap engagement of the retention member onto the abutment and may be swiveled or rotated into place through use of the swivel joint between the cap and retention member, which is further enhanced by the concave recess within the cap.

FIG. 14 is a side view illustration of the dental attachment assembly after securing a dental appliance 120 with the cap 108 in the abutment 104 attached with the implant 102 in a patient's mouth 122. FIG. 15 is a side view illustration of the method of attaching the dental appliance 120 to the cap 108 and retention member 106, and subsequently fitting the dental appliance assembly onto the abutment 104 and implant 102.

By providing the cap with the concave recess in combination with multiple configurations of the dental attachment assembly, any dental attachment assembly is provided with an increased allowable angle correction when attaching a dental appliance to an implant, simplifying the attachment process and reducing the risk of damage to the component parts from misalignments and wear from use at high angulations.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A dental attachment assembly comprising:
   an abutment member with a first end shaped to attach to a tooth root, implant or adjacent tooth, and a second end with an outer locating surface, wherein the outer locating surface of the abutment member has at least two axially spaced retention portions comprising two generally rounded, annular projections;
   a retention member having a first end and a skirt extending from the first end defining an inner surface for engagement over the outer locating surface of the abutment member, wherein the retention member has at least two axially spaced, snap engaging formations on the inner surface of the skirt for releasable snap engagement with the respective retention portions of the abutment member, and wherein the axially spaced, snap engaging formations on the inner surface of the skirt comprise two spaced, annular grooves for snap engagement over the annular projections on the abutment member; and
   a cap with a rounded, concave inner surface defining a cavity to receive a swivel engagement with the retention member; wherein an interior top surface of the cavity includes a concave recess extending radially along an outer periphery of the interior top surface of the cavity.

2. The dental attachment assembly of claim 1, further comprising a central portion of the interior top surface which protrudes vertically into the cavity.

3. The dental attachment assembly of claim 2, wherein the retention member is in direct contact with the central portion of the interior top surface.

4. The dental attachment assembly of claim 1, wherein a curve of the concave recess continues along a side wall of the rounded, concave inner surface of the cavity.

5. The dental attachment assembly of claim 4, wherein the concave recess curves at a plurality of varying angles along the side wall and the interior top surface of the cavity.

6. The dental attachment assembly of claim 4, wherein the concave recess is composed of a series of consecutive tangent circular arcs.

7. The dental attachment assembly of claim 6, wherein the series of consecutive tangent circular arcs increase in size from the interior top surface to the bottom portion of the cap.

8. The dental attachment assembly of claim 7, wherein the series of consecutive tangent circular arcs are comprised of circles of increasing size from a top portion of the cap to a bottom portion of the cap.

9. The dental attachment assembly of claim 1, wherein an outer diameter of the cap is approximately 5.4 millimeters (mm) and a height of the cap is approximately 2.3 mm.

10. The dental attachment assembly of claim 1, wherein the concave recess provides a retention member with an angle correction of up to approximately 30 degrees.

\* \* \* \* \*